(12) United States Patent
Kahler et al.

(10) Patent No.: US 11,253,238 B2
(45) Date of Patent: Feb. 22, 2022

(54) SENSOR DETECTION SYSTEM (71) Applicant: Aesculap AG, Tuttlingen (DE)

(72) Inventors: Thomas Kahler, Seitingen-Oberflacht (DE); Roland-Alois Högerle, Tuttlingen (DE); Martin Machill, Rietheim-Weilheim (DE)

(73) Assignee: AESCULAP AG, Tuttlingen (DE)

( * ) Notice: Subject to any disclaimer, the term of this patent is extended or adjusted under 35 U.S.C. 154(b) by 593 days.

(21) Appl. No.: 16/088,650

(22) PCT Filed: Mar. 28, 2017

(86) PCT No.: PCT/EP2017/057311
§ 371 (c)(1),
(2) Date: Sep. 26, 2018

(87) PCT Pub. No.: WO2017/167749
PCT Pub. Date: Oct. 5, 2017

(65) Prior Publication Data
US 2020/0297332 A1 Sep. 24, 2020

(30) Foreign Application Priority Data
Mar. 30, 2016 (DE) .................... 10 2016 105 789.4

(51) Int. Cl.
*A61B 17/00* (2006.01)
(52) U.S. Cl.
CPC .... *A61B 17/00* (2013.01); *A61B 2017/00017* (2013.01); *A61B 2017/00039* (2013.01);
(Continued)

(58) Field of Classification Search
CPC .......... A61B 17/00; A61B 2017/00017; A61B 2017/00039; A61B 2017/00057; A61B 2017/00398
(Continued)

(56) References Cited

U.S. PATENT DOCUMENTS 6,090,122 A 7/2000 Sjostrom et al.
6,659,870 B2 * 12/2003 Sobota .................... A63F 13/06
463/37
(Continued)

FOREIGN PATENT DOCUMENTS

AT 007217 U1 11/2004
DE 202009007437 U1 8/2009
(Continued)

OTHER PUBLICATIONS

German Search Report for German Application No. 10 2016 105 789.4, dated Dec. 13, 2016, with translation—16 pages.
(Continued)

*Primary Examiner* — Aaron F Roane (57) ABSTRACT

A detector system for a medical motor system includes a multi-channel redundantly-configured detection device, which is accommodated in a hand-held control device that is adapted to control the medical motor system and which is positioned to detect the actuation of an actuation device of the hand-held control device. The multi-channel redundantly-configured detection device allows the plausibility of its output signals to be checked.

10 Claims, 4 Drawing Sheets

(52) U.S. Cl.
CPC .............. *A61B 2017/00057* (2013.01); *A61B 2017/00398* (2013.01)

(58) Field of Classification Search
USPC ............................................................ 606/1
See application file for complete search history.

(56) References Cited

U.S. PATENT DOCUMENTS

| | | | | |
|---|---|---|---|---|
| 2005/0021078 | A1* | 1/2005 | Vleugels | A61B 34/76 606/205 |
| 2012/0116391 | A1 | 5/2012 | Houser et al. | |
| 2014/0012238 | A1* | 1/2014 | Chen | A61B 17/10 606/1 |
| 2014/0200594 | A1 | 7/2014 | Vidal et al. | |

FOREIGN PATENT DOCUMENTS

| | | |
|---|---|---|
| DE | 102012201379 A1 | 8/2013 |
| EP | 2671690 A1 | 12/2013 |
| EP | 2923651 A1 | 9/2015 |
| EP | 2992842 A1 | 3/2016 |
| JP | 2000508183 A | 7/2000 |
| JP | 2014529437 A | 11/2014 |
| WO | 2007002180 A2 | 1/2007 |
| WO | 2007002180 A3 | 8/2007 |
| WO | 2013026922 A1 | 2/2013 |

OTHER PUBLICATIONS

International Search Report and Written Opinion for International Application No. PCT/EP2017/057311, dated Jun. 1, 2017—9 pages.
Office Action received in Japanese Application No. 2018-550468 dated Apr. 1, 2021, with translation, 10 pages.
Extended European Search Report received in European Application No. 21181118.7-1122 dated Sep. 24, 2021, with translation, 33 pages.

* cited by examiner

SENSOR DETECTION SYSTEM

RELATED APPLICATION(S)

This application is the United States national phase entry of International Application No. PCT/EP2017/057311, filed Mar. 28, 2017, which claims the benefit of priority of German Application No. 10 2016 105 789.4, filed Mar. 30, 2016. The contents of International Application No. PCT/EP2017/057311 and German Application No. 10 2016 105 789.4 are incorporated by reference herein in their entireties.

FIELD

The invention relates to a sensor detector system and concerns in particular a sensor detector system for a medical, in particular surgical motor system or a medical, in particular surgical electrical drive.

BACKGROUND

A well-known sensor detector system for a surgical motor system is a single-channel, non-redundant detector system using, for example, a Hall sensor for electrical systems, which is also used, among other things, in a known motor cable with manual control. Until now, such electrical systems have used mechanical return springs that return an actuating device such as a lever or a slider to its initial position after having been actuated by a user. If a wrong signal is unintentionally output from a sensor of the detector system, a safety-relevant malfunction may occur. If, for example, the sensor suddenly fails, for example due to a stuck-at-fault error or adhesion error of the sensor (an error in which, for example, a sensor gate is "stuck" at a certain value at an input or output), an application part or tool can get activated or start without a user actuating the actuating device. This can surprise the user who is in or near a surgical site with the application part and/or tool, for example. A disadvantage of the non-redundant detector system is that an electronic failure is not safeguarded.

SUMMARY

The invention is therefore based on the object of improving a sensor detector system for a medical or surgical motor system or a medical or surgical electrical drive in such a way that a plausibility check of the signals is made possible and the safety of the system is increased.

The invention is based on the general idea of providing multi-channel and thus redundant signals and/or detector systems in hand-held controls. The use of at least two sensors, which are controlled independently of each other but parallel (simultaneously), ensures that in the event of failure of at least one sensor, an error or defect is detected and the hand-held control can be deactivated by an external control unit, to which the hand-held control is usually connected. According to the underlying general idea, the output signals or output signal values of the at least two sensors can be programmed the same or different, the sensors can preferably be controlled by means of a magnetic field or magnetically and in this case by means of a magnet for all sensors, by means of several magnets for respective sensor groups or by means of individual magnets for each respective sensor. In addition, the magnet(s) and/or the sensor(s) may be encapsulated, e.g. potted, for achieving water and/or vapor tightness. Furthermore, the sensor(s) may be fixedly arranged in a device and the magnet(s) may move toward the sensor(s), e.g. in the form of a circular arc in the case of a hinge device, for example, or linear. However, there is no limitation in regards to a motion path and/or direction of motion; in principle, movements in any directions and/or on any motion paths are conceivable. Finally, several and at least two independent sensors may be integrated in a module with several or at least two independent, integrated sensor ranges.

The use of a redundant sensor detector system for hand- and/or foot-operated controls provides increased safety against unwanted and unintentional starting of an application part or tool and thus prevents the starting of appropriate devices and thus injuries to sensitive tissue when the tool is in the surgical site.

Specifically, a sensor detector system for a medical motor system comprises a multi-channel redundantly-configured detection device which is accommodated in a hand-held control device that is adapted to control the medical motor system and which is arranged to detect the actuation of an actuating device of the hand-held control device, wherein the multi-channel redundant detection device is designed to allow the plausibility of its output signals to be checked.

The multi-channel redundant detection device preferably comprises at least two detection receiving devices and at least one detection transmitting device.

The at least two detection receiving devices are preferably of the same type.

The at least one detection transmitting device preferably comprises exactly one detection transmitting device which is assigned to all of the at least two detection receiving devices and is arranged to charge these with a detection transmitting quantity which is basically the same.

Alternatively, an associated detection transmitting device is preferably provided for each of the at least two detection receiving devices and is arranged to charge a corresponding one of the at least two detection receiving devices with a respective detection transmitting quantity.

At least two Hall sensors are preferably arranged as the at least two detection receiving devices and at least one magnet is arranged as the at least one detection transmitting device.

Alternatively, at least two light sensors are preferably arranged as the at least two detection receiving devices and at least one light source is arranged as the at least one detection transmitting device.

Alternatively, it is preferred that the at least two detection receiving devices are different detection receiving devices.

In the latter case, it is preferred that two detection receiving devices and two detection transmitting devices are arranged, one of the two detection receiving devices being a Hall sensor and the other of the two detection receiving devices being a light sensor, and one of the two detection transmitting devices being a magnet associated with the Hall sensor and the other of the two detection transmitting devices being a light source associated with the light sensor.

Preferably, the at least two detection receiving devices, each with mutually independent detection ranges, are accommodated in a common housing assembly.

Preferably, the at least two detection receiving devices and/or the at least one detection transmitting device are encapsulated in a vapor-proof and/or watertight manner.

Preferably, the at least two detection receiving devices are stationarily positioned and the at least one detection transmitting device is movably positioned and can be moved toward and away from the at least two detection receiving devices by actuating the actuating device on a predetermined trajectory.

Preferably, the at least two detection receiving devices are programmed to output the same output signal or are alternatively programmed to output different output signals.

Advantageously, a hand-held control device for a medical motor system comprises a detector system configured as described above.

In other words, the object is achieved by a detector system for a medical motor system, comprising a multi-channel redundantly-configured detection device which is accommodated in a hand-held control device that is adapted to control the medical motor system and which is positioned to detect the actuation of an actuating device of the hand-held control device, wherein the actuation device is configured as a lever or slider;
the multi-channel redundant detection device comprises at least two detection receiving devices and exactly one detection transmitting device;
the exactly one detection transmitting device is associated with all of said at least two detection receiving devices and arranged to charge these with a detection transmitting quantity which is basically the same; and
the multi-channel redundant detection device is designed to allow the plausibility of its output signals to be checked.

Preferably, the detector system is further developed such that the at least two detection receiving devices are positioned so as to be offset in the direction of a lever path or slider path of the exactly one detection transmitting device.

Preferably, the detector system is further developed such that the at least two detection receiving devices comprise Hall sensors or light sensors and the exactly one detection transmitting device comprises a magnet or a light source.

Preferably, the detector system is further developed such that the at least two detection receiving devices are similar detection receiving devices.

Preferably, the detector system is further developed such that an associated detection transmitting device is provided for each of the at least two detection receiving devices and is arranged to charge a corresponding one of the at least two detection receiving devices with a respective detection transmitting quantity.

Preferably, the detector system is further developed such that the at least two detection receiving devices are different detection receiving devices.

Preferably, the detector system is further developed such that the at least two detection receiving devices, each with mutually independent detection ranges, are accommodated in a common housing assembly.

Preferably, the detector system is further developed such that the at least two detection receiving devices and/or the exactly one detection transmitting device are encapsulated in a vapor-proof and/or watertight manner.

Preferably, the detector system is further developed such that the at least two detection receiving devices are stationarily positioned and the exactly one detection transmitting device is movably positioned and can be moved toward the at least two detection receiving devices by actuating the actuating device on a predetermined trajectory.

Preferably, the detector system is further developed such that the at least two detection receiving devices are programmed to output the same output signal or are programmed to output different output signals.

Furthermore, the object is achieved by a hand-held control device for a medical motor system, comprising a detector system as defined above.

BRIEF DESCRIPTION OF THE DRAWING FIGURE(S)

The invention is described in more detail below with further advantages and effects on the basis of preferred exemplary embodiments with reference to the drawing in which.

Identical or functionally equivalent characteristics have the same reference signs in the individual figures and expediently are not described in a redundant way.

DETAILED DESCRIPTION

Figure 1:
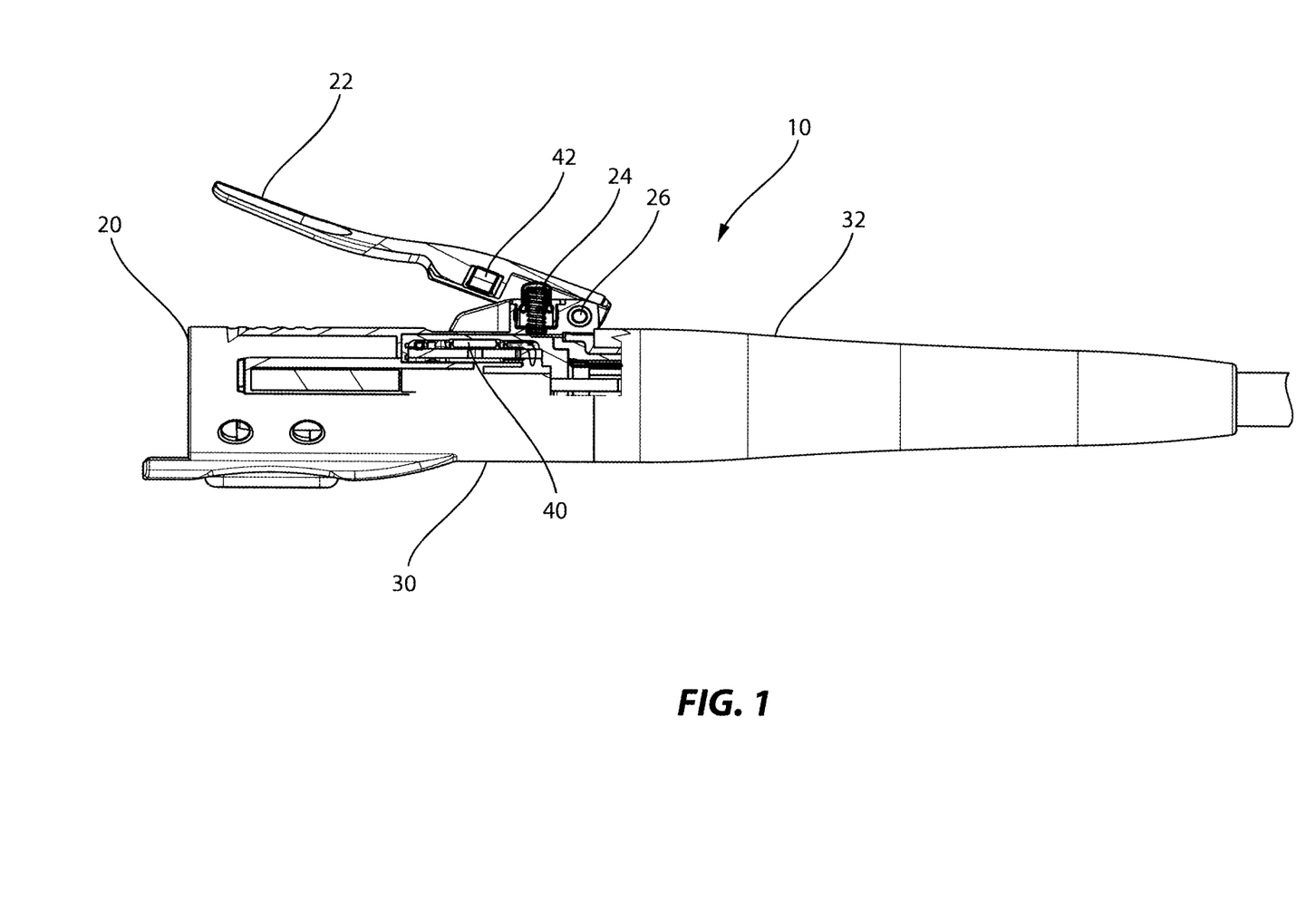
FIG. 1 is a schematic representation of a hand-held control device of a medical or surgical motor system with a lever operation unit that includes a sensor detector system according to one of exemplary embodiments described herein.

FIG. 1 shows a schematic representation of a hand-held control device 10 of a medical or surgical motor system with a lever operation unit that includes a sensor detector system according to one of exemplary embodiments described herein.

With the exception of the differences according to one of the following exemplary embodiments, such a hand-held control device 10 is known on principle and essentially comprises an application-side motor cable connector 20 for supplying and controlling the electronic motor system (which is integrated, for example, in the handpiece) via e.g. a (not shown) external control unit, a manually operable lever 22 which is spring-loaded by means of a mechanical return spring 24 which serves to return the non-actuated lever 22 to the output position, and is articulated on a lever axle 26 on a housing body 30 of the hand-held control device 10 so as to be able to pivot. On the output side, there is a cable arrangement with a bend protection sheath 32, on which a medical tool driven by the motor of the motor system, such as a cutter for treatment in the surgical site, is engaged. Such systems can be used in areas such as bone surgery and arthroscopy, neurosurgery, veterinary medicine and the like, without being limited thereto.

Figure 2:
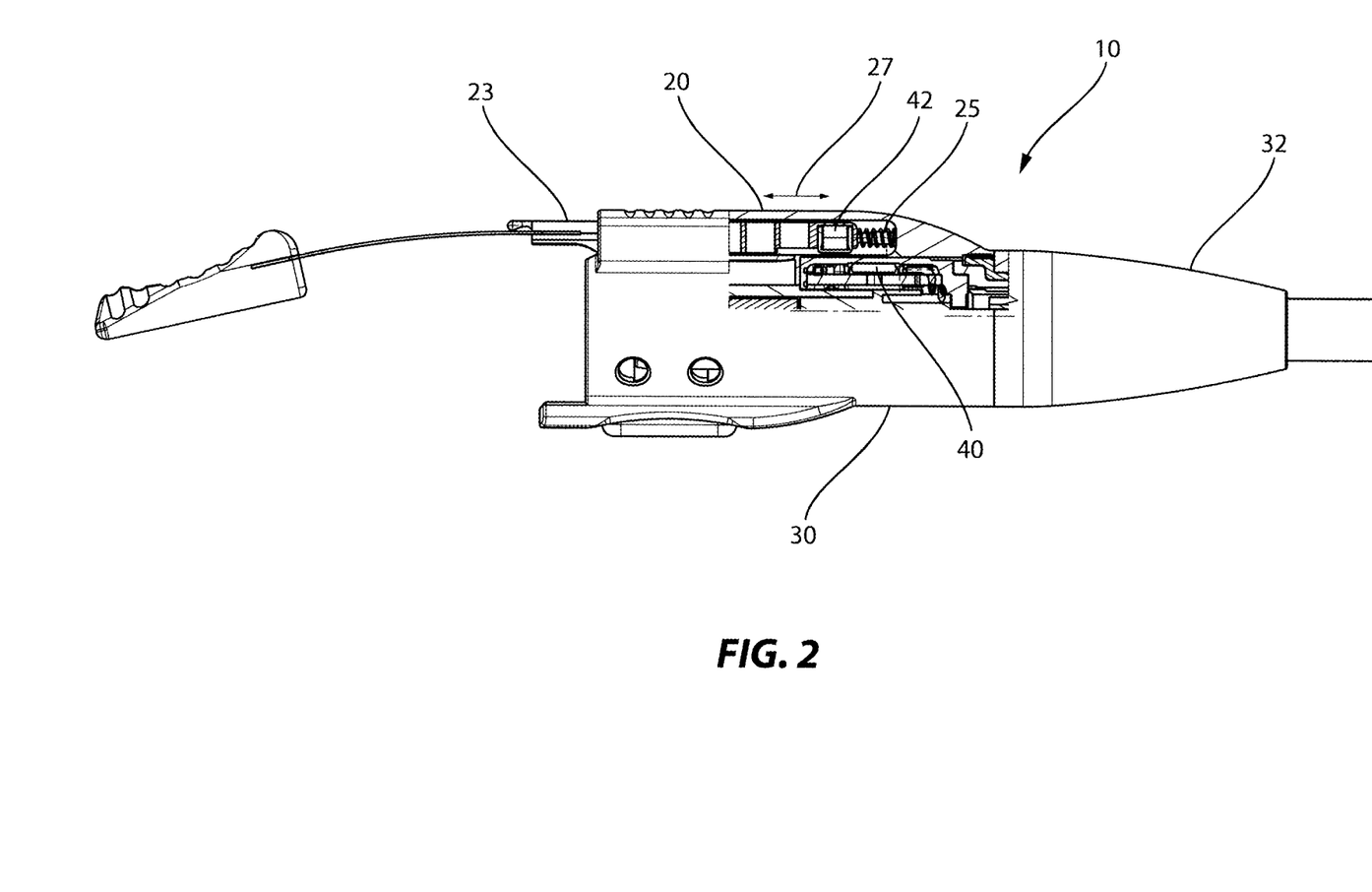
FIG. 2 is a schematic representation of a hand-held control device of a medical or surgical motor system with a slider operation unit that includes a sensor detector system according to one of exemplary embodiments described herein.

FIG. 2 shows a schematic representation of a hand-held control device of a medical or surgical motor system with a slider operation unit that includes a sensor detector system according to one of exemplary embodiments described herein.

In contrast to the hand-held control device according to FIG. 1, in the embodiment according to FIG. 2 a slider 23 is provided instead of the lever 22 for the manual activation of the electronic motor system, which slider is spring-loaded by means of a mechanical return spring 25 serving to return the unloaded slider 23 to the initial position, and which is articulated so as to be able to be moved along a displacement path 27 on a housing body 30 of the hand-held control device 10.

In accordance with the present exemplary embodiments, the hand-held control device 10 according to FIG. 1 or FIG.

2 also has a detector system for the medical or surgical motor system which comprises a multi-channel redundantly-configured detection device which is accommodated in the hand-held control device 10 adapted to control the medical motor system and which is positioned to detect the actuation of the lever 22 or the slider 23 of the hand-held control device 10, wherein the multi-channel redundantly-configured detection device is designed to allow the plausibility of output signals from sensors 40 arranged in the sensor system to be checked.

In detail, the multi-channel redundant detection device comprises at least two sensors 40 in accordance with the present exemplary embodiments, which each form detection receiving devices and may be designed as Hall sensors and/or optical sensors in the form of, for example, light sensors, and at least one variable sender or (variable) transmitter 42 acting on the sensors 40, which forms a detection transmitting device and may accordingly be designed as a magnet with respective magnetic north and south poles or as a light source emitting light in the visible or invisible range, for example infrared range.

The at least two sensors 40 and the at least one transmitter 42 form a multi-channel (redundant) (signal) detector system which serves to protect the hand-held control device 10 against the tool running without the user's request. In other words, the overall assembly is designed to prevent an application part or tool from starting or running by means of the multi-channel redundant detector system when a fault is detected and/or without the lever 22 or the slide 23 being actuated by a user. Therefore, even in a case in which one of the sensors 40 suddenly becomes defective, a status inquiry or signal plausibility inquiry based on the at least two output signals of the at least two sensors 40 allows to detect an error state and, by triggering a switch-off of the hand-held control device 10, prevent the user having an application part/tool in the surgical site from being surprised by a sudden start of the tool. By using at least two sensors 40, which are controlled independently of each other but in parallel (at the same time), it is ensured that if one sensor 40 fails, the defect is detected and the hand-held control device 10 can be deactivated by the control unit.

With a correspondingly adapted status or signal plausibility inquiry, the at least two sensors 40 may be arranged for outputting basically the same output signal, for example if the at least two sensors 40 are identical or of the same type or construction, or alternatively for the output of different output signals, for example if the at least two sensors 40 are of different type or construction. If, for example, the individual sensors 40 each deliver output signals that deviate in their combination from predetermined plausible states or plausibility conditions, it can be concluded that an error state is present.

In one exemplary embodiment, exactly one transmitter 42 may be provided which is assigned to all of the at least two sensors 40 and is arranged to charge them with a detection transmission variable which is basically the same. In this case, both sensors 40 receive or detect the basically identical signal or a corresponding variable of one and the same transmitter 42, for example a magnet or a light source.

Alternatively, each of the at least two sensors 40 may have a transmitter 42 individually assigned to each sensor 40, which is arranged to supply its respective signal or variable to the corresponding sensor 42 assigned to it.

In an exemplary embodiment, at least two Hall sensors are arranged as the at least two sensors 40 and at least one magnet is arranged as the at least one transmitter 42. In another exemplary embodiment, at least two light sensors are arranged as the at least two sensors 40 and at least one light source is arranged as the at least one transmitter 42.

In the case where the at least two sensors 40 are of different design or are arranged to detect different (physical) quantities, two sensors 40 and two transmitters 42 may be arranged in another exemplary embodiment, with one of the two sensors 40 being a Hall sensor and the other of the two sensors 40 being a light sensor, and one of the two transmitters 40 being a magnet associated with the Hall sensor, and the other of the two transmitters 42 being a light source associated with the light sensor.

In a further exemplary embodiment, the at least two sensors 40 each having independent detection ranges may be accommodated in a common housing assembly. In addition, individually provided sensors 40 and/or sensors 40 installed in a common housing assembly may each be encapsulated in a vapor- and/or watertight manner, for example glued or potted.

In the hand-held control device 10 shown in FIG. 1, the at least two sensors 40 are preferably accommodated and positioned to be stationary in the handle or handpiece, and the at least one transmitter 42 is positioned to be movable in the lever 22 and can be moved to and away from the at least two sensors 40 by actuating (pressing down or releasing) the lever 22 on a predetermined trajectory. In other words, actuating the lever 22 by pressing it down causes the at least one transmitter 42 to approach the at least two sensors 40, so that they detect its output variable (in the present exemplary embodiment, for example, a magnetic variable or a luminous flux) and, for example, switch when a threshold value is exceeded or change their output signal, and operating the lever 22 in the opposite direction by releasing it causes the at least one transmitter 42 to move away from the at least two sensors 40 and weaken the signal detectable by them. On the basis of the lever geometry, the movement of the transmitter 42 follows in each case a predetermined movement path or trajectory.

In the hand-held control device 10 shown in FIG. 2, the at least two sensors 40 are preferably accommodated and positioned so as to be stationary in the handle or handpiece, and the at least one transmitter 42 is arranged in the displacement path 27 between the slider 23 and the return spring 25 such that an actuation of the slider 23 results in a displacement of the transmitter 42 in a first direction and a release of the slider 23, due to the restoring force of the return spring 25, leads to a displacement of the transmitter 42 in a second direction opposite to the first direction. In other words, when the slider 23 is actuated/released, the at least one transmitter 42 is moved back and forth along the displacement path 27 towards or away from the at least two sensors 40, which are positioned in a suitable positional relationship, so that they detect the output variable of the at least one transmitter 42 (in the present exemplary embodiment, for example, a magnetic variable or a luminous flux) and perform a switching process or change their output signal, for example, when a threshold value is exceeded or the detectable variable is attenuated. Here too, the displacement path 27 corresponds to a predetermined trajectory along which the at least one transmitter 42 is movable.

Figure 3:
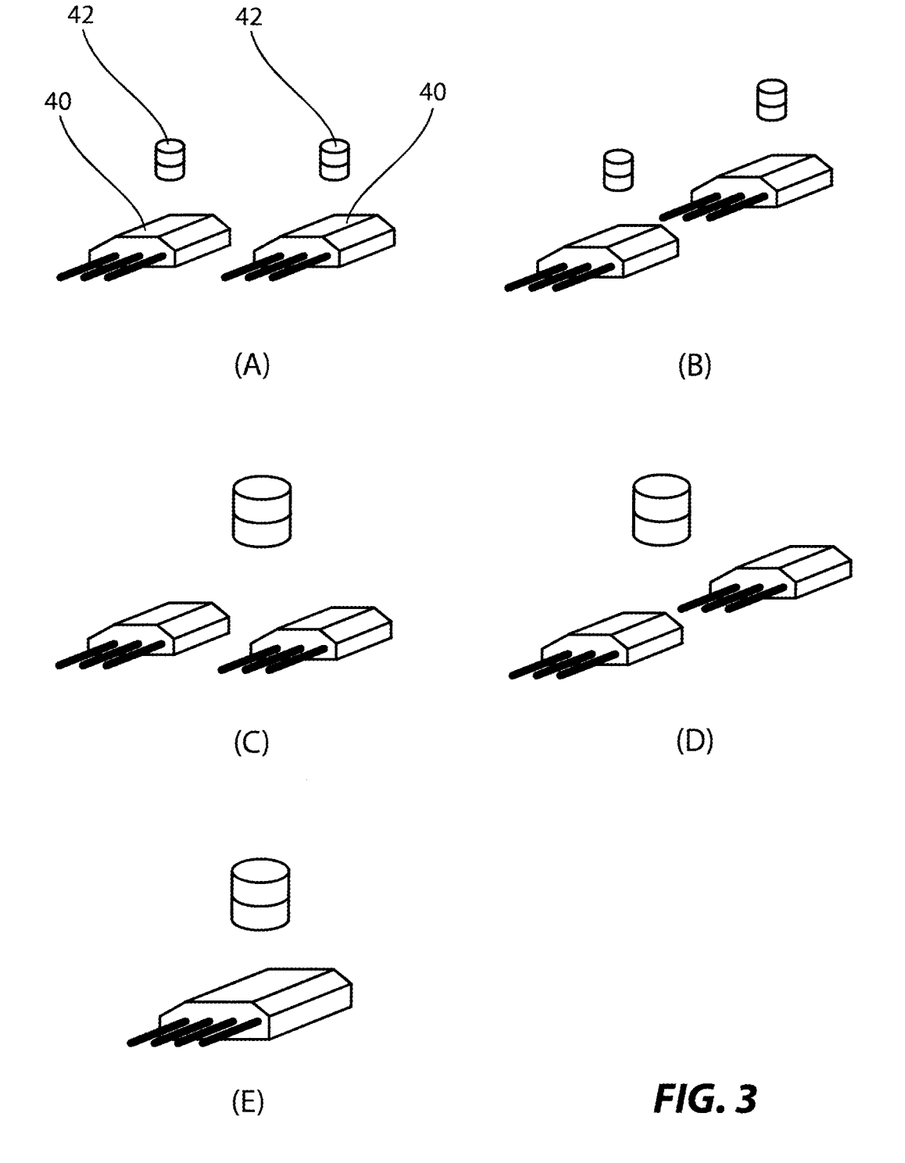
FIG. 3 is a basic principle of arrangements using the example of a sensor detector system based on magnets and magnetically influenced sensors.

FIG. 3 shows a basic diagram of a number of possible sensor/transmitter arrangements using the example of the sensor detector system based on magnets and magnetically influenced sensors on the basis of various exemplary embodiments. The number of arrangements is not limited to the number shown, so that other designs may also result in relation to the case of application and/or in a specific practical embodiment.

FIG. 3(A) shows a case in which two sensors 40 (Hall sensors) and two transmitters 42 (magnets) are positioned side by side. In this case, each of the transmitters 42 individually acts on the sensor 40 associated to it. FIG. 3(B) shows a case in which two sensors 40 (Hall sensors) and two transmitters 42 (magnets) are positioned one behind the other. In this case too, each of the transmitters 42 individually acts on the sensor 40 associated to it. FIG. 3(C) shows a case in which two sensors 40 (Hall sensors) are positioned side by side and for both sensors 40 a shared transmitter 42 (magnet) is provided. Here, the single transmitter 42 acts on both sensors 40 associated to it. FIG. 3(D) shows a case in which two sensors 40 (Hall sensors) are positioned one behind the other and for both sensors 42 a common transmitter 42 (magnet) is provided. Here too, the transmitter 42 acts on both sensors 40 associated to it. FIG. 3(E) finally shows a case in which two sensors 40 are accommodated in a common sensor housing and a common transmitter 42 is assigned to them.

It is noted that in FIG. 3(A) to 3(D), i.e. in the case of two sensors 40 with two magnets or transmitters 40, a total of three dedicated sensor terminals may be provided as terminals at each sensor 40, i.e. a respective terminal for ground, supply voltage and output or output (signal), and in FIG. 3(E), i.e. a double sensor with a magnet or transmitter 42, a total of four dedicated sensor terminals may be provided as terminals for ground, supply voltage and output 1 or output (signal) 1 and output 2 or output (signal) 2.

Figure 4:
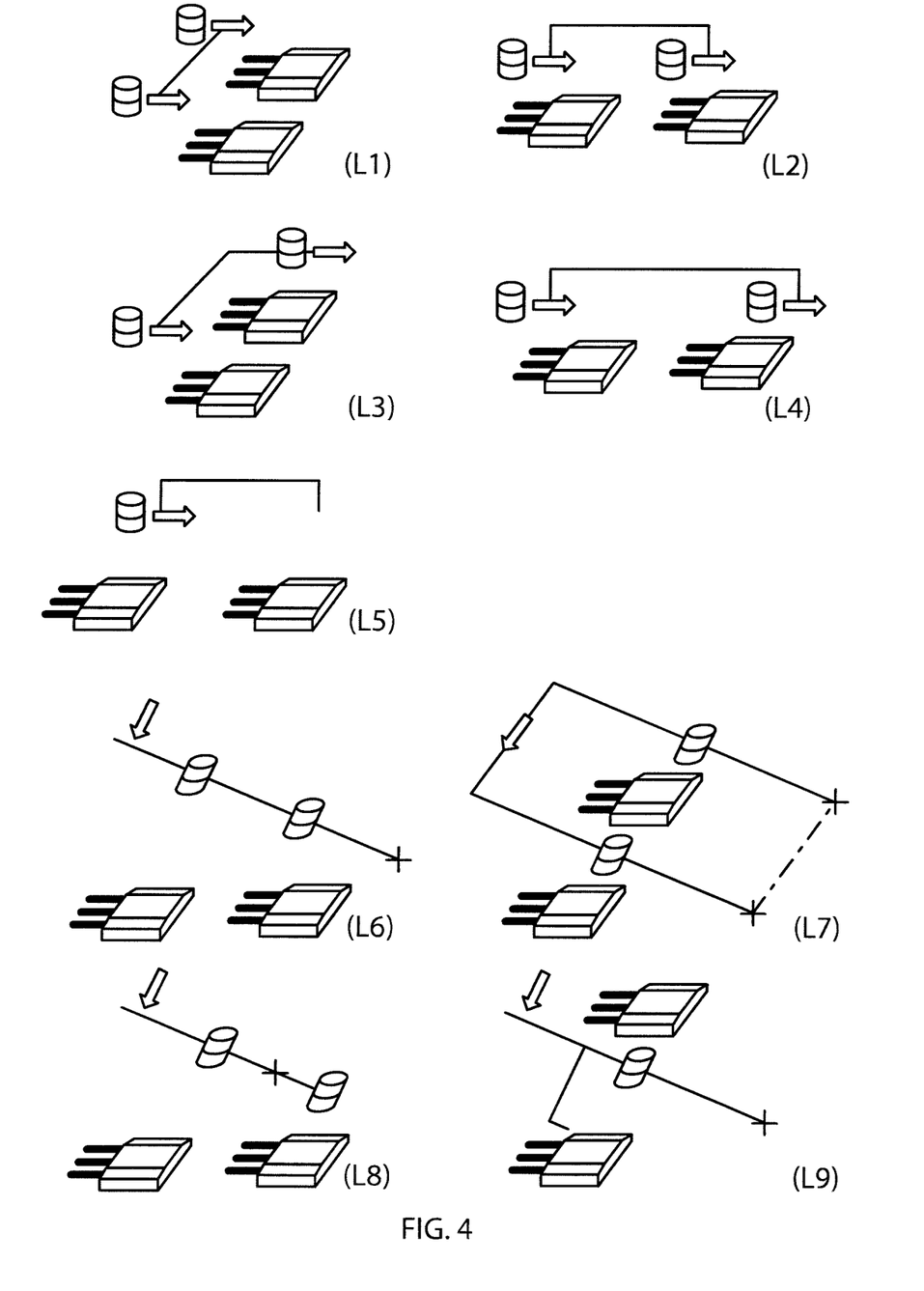
FIG. 4 is a basic principle of concepts for hand-held control devices using the arrangements according to FIG. 3.

FIG. 4 shows a basic principle of concepts for hand-held control devices (here using the lever 22 or slider 23) using the arrangements and/or exemplary embodiments according to FIG. 3.

In detail, FIG. 4(L1) to FIG. 4(L5) show slider-based control devices (parallel: (L1), (L2); offset: (L3), (L4), (L5)) each having one or two transmitters 42, in which the at least one movably positioned transmitter 42 is displaceable by means of the slider 23 (FIG. 2) along an imaginary line in the direction of an arrow also shown (and opposite thereto), i.e. toward the at least two stationarily positioned sensors 40 or away from them for an opposite process.

FIG. 4(L6) to (L9) illustrate lever-based control devices (parallel: (L6), L(7); offset: (L8), L(9)) each comprising one or two transmitters 42, in which the at least one movably provided transmitter 42 can be pivoted by the lever 22 (FIG. 1) toward the at least two stationarily positioned sensors 40 or away from them for an opposite process. The cross symbol shown in each of the FIGS. 4(L6) to (L9) represents a pivot point or axis of rotation of the lever 22, around which the at least one transmitter 42 arranged along an imaginary line can be pivoted in the direction of the arrow shown (and in the direction opposite thereto).

It is noted that in FIG. 4 the at least one transmitter 42 is shown as being movable and the at least two sensors 40 are shown as being stationary. However, the invention is not necessarily limited to this. Rather, it is also possible to make a configuration in which the at least one transmitter 42 is arranged to be stationary and the at least two sensors 40 are arranged to be movable.

Further exemplary embodiments include combinations of different sensor types. In other words, different sensor types may also be combined in the possible individual arrangement systems as described above comprising two Hall sensors as receiver or sensor 40 and two magnets as transmitter 42. For example, in the cases of FIG. 4 (L1) to FIG. 4(L9), the two Hall sensors may be replaced by two light systems (light transmitter and light receiver) whose light emissions may be in the visible or invisible range, for example the infrared range. In these cases, an associated light source, as the at least one transmitter 42, may be concealed, encapsulated and protected behind transparent materials, such as opaque or clear plastics or glass, or behind a material that is clear to dark in terms of transparency but permeable to infrared.

Alternatively, at least in the cases of FIG. 4(L1) to FIG. 4(L4) and FIG. 4(L6) to FIG. 4(L8), i.e. in those cases in which a transmitter 42 is directly assigned to each sensor 40 and therefore the transmitter 42 does not move from one sensor to another sensor 40, only one of the two Hall sensors may be replaced by such a light system.

Furthermore, in the arrangements described above, it is possible to provide the at least two sensors 40 completely in analogue version, completely in digital version or in a combination of analogue version and digital version.

Thus, a redundant detector system has been described above for an electric hand-held control device, which is preferably in the form of a housing assembly with at least two sensor elements and at least one magnet, which are thus designed with at least two channels in order to stop the function of the hand-held control device in the event of faulty signals detected by at least double (redundant) interrogation, i.e. a malfunction such as a start without request, and thereby ensure that an unintentional activation or an unintentional continued run of application parts (e.g. in the surgical site) is prevented. The detector system may thus be designed for a medical and/or surgical motor system and include a multi-channel redundant detection device which is accommodated in a hand-held control device adapted to control the medical motor system and which is positioned to detect the actuation of an actuating device of the hand-held control device, wherein the multi-channel redundant detection device is designed to allow the plausibility of its output signals being checked.

It is understood that the described exemplary embodiments and the drawings not to scale are only exemplary in character and that modifications may easily result for the person skilled in the art without the scope according to the description and the scope of protection defined by the attached claims being left behind. Likewise, external shapes, dimensions and the like are not subject to any special restrictions as long as the effect and functionality according to the invention are provided and achieved by them.

The invention claimed is:

1. A detector system for a medical motor system, comprising a multi-channel redundant detection device which is accommodated in a hand-held control device that is adapted to control the medical motor system and which is positioned to detect actuation of an actuating device of the hand-held control device, wherein
    the actuation device is configured as a lever or slider;
    the multi-channel redundant detection device comprises at least two detection receiving devices and exactly one detection transmitting device;
    the exactly one detection transmitting device associated with all of said at least two detection receiving devices and arranged to charge said at least two detection receiving devices with a detection transmitting quantity which is equal;
    the multi-channel redundant detection device is designed to allow the plausibility of its output signals to be checked; and
    the at least two detection receiving devices and/or the exactly one detection transmitting device are each individually encapsulated in a vapor-proof and/or watertight manner to protect the at least two detection receiving devices and/or the exactly one detection transmitting device from water or vapor present in the hand-held control device.

2. The detector system according to claim 1, wherein the at least two detection receiving devices are positioned so as to be offset in a direction of a lever path or slider path of the exactly one detection transmitting device.

3. The detector system according to claim 2, wherein the at least two detection receiving devices comprise Hall sensors or light sensors and the exactly one detection transmitting device comprises a magnet or a light source.

4. The detector system according to claim 1, wherein the at least two detection receiving devices are identical detection receiving devices.

5. The detector system according to claim 1, wherein the at least two detection receiving devices are different detection receiving devices.

6. The detector system according to claim 1, wherein the at least two detection receiving devices, each with mutually independent detection ranges, are accommodated in a common housing assembly.

7. The detector system according to claim 1, wherein the at least two detection receiving devices are stationarily positioned and the exactly one detection transmitting device is movably positioned and movable toward the at least two detection receiving devices by actuating the actuating device on a predetermined trajectory.

8. The detector system according to claim 1, wherein the at least two detection receiving devices are programmed to output a same output signal or are programmed to output different output signals.

9. A hand-held control device for a medical motor system, comprising a detector system according to claim 1.

10. A detector system for a medical motor system, comprising a multi-channel redundant detection device which is accommodated in a hand-held control device that is adapted to control the medical motor system and which is positioned to detect actuation of an actuating device of the hand-held control device, wherein:

the actuation device is configured as a lever or slider;

the multi-channel redundant detection device comprises a first detection receiving device, a second detection receiving device, a first detection transmitting device associated with the first detection receiving device, and a second detection transmitting device associated with the second detection receiving device, the second detection transmitting device being distinct from the first detection transmitting device; and the multi-channel redundant detection device is designed to allow the plausibility of its output signals to be checked, in which the first detection transmitting device is provided for the first detection receiving device and is arranged to charge the first detection receiving device with a first detection transmitting quantity, and the second detection transmitting device is provided for the second detection receiving device and is arranged to charge the second detection receiving device with a second detection transmitting quantity, wherein the first and second detection receiving devices, each with mutually independent detection ranges, are accommodated in a common housing assembly, and wherein the first and second detection receiving devices and/or the first and second detection transmitting devices are individually encapsulated in a vapor-proof and/or watertight manner to protect the first and second detection receiving devices and/or the first and second detection transmitting devices from water or vapor present in the common housing assembly.

\* \* \* \* \*